United States Patent [19]

Zimmerman et al.

[11] 4,219,652

[45] Aug. 26, 1980

[54] N-METHYL AND N-PHENETHYL-CIS-DECAHYDROISOQUINOLINES

[75] Inventors: Dennis M. Zimmerman, Morresville; Winston S. Marshall, Bargersville, both of Ind.

[73] Assignee: Eli Lilly and Company, Indianapolis, Ind.

[21] Appl. No.: 618,175

[22] Filed: Sep. 30, 1975

Related U.S. Application Data

[63] Continuation-in-part of Ser. No. 467,707, May 7, 1974, Ser. No. 477,221, Jun. 7, 1974, abandoned, and Ser. No. 487,342, Jul. 10, 1974, abandoned.

[51] Int. Cl.$^2$ .................... C07D 217/16; A61K 31/47
[52] U.S. Cl. ...................................... 546/144; 424/258
[58] Field of Search .................... 260/289 D; 546/144

[56] References Cited

U.S. PATENT DOCUMENTS 4,001,247   1/1977   Zimmerman et al. ........... 260/289 D

FOREIGN PATENT DOCUMENTS 802557   1/1974   Belgium .............................. 260/289 D
833212   3/1976   Belgium .............................. 260/289 D

OTHER PUBLICATIONS

Sugimoto et al., Chem. Abst., 50, 1814f (1956).
Finch et al., "J. Org. Chem.", 39, pp. 1118–1124 (1974).
Boekelheide et al., J.A.C.S., vol. 72, pp. 712–715 (1950).

Primary Examiner—Glennon H. Hollrah
Assistant Examiner—D. B. Springer
Attorney, Agent, or Firm—James L. Rowe; Everet F. Smith

[57] ABSTRACT

1-Methyl and 1-phenethyl-3a-hydroxy or alkoxy phenyl-cis-decahydroisoquinolines, useful as analgetics.

4 Claims, No Drawings

N-METHYL AND N-PHENETHYL-CIS-DECAHYDROISOQUINOLINES

CROSS-REFERENCE

This application is a continuation-in-part of our co-pending application Ser. No. 467,707, filed May 7, 1974, Ser. No. 477,221, filed June 7, 1974, abandoned and Ser. No. 487,342 filed July 10, 1974 abandoned.

BACKGROUND OF THE INVENTION

It has long been known that slight chemical modifications of the morphine molecule lead to analgesic agonists of widely differing potency and addictive properties. For example, codeine, the methyl ether of morphine, is a relatively mild analgesic agonist having slight dependance (addiction) liability. On the other hand, heroin, the diacetyl derivative of morphine, is a powerful agonist with extremely high addiction potential. In addition, as long ago as 1915, Pohl found that when the N-methyl group of codeine was replaced with an allyl group, the resulting compound, N-allylnorcodeine, was an opiate antagonist. In 1940, N-allylnormorphine or nalorphine was synthesized and was shown to have a highly specific ability to reverse the depressant effects of morphine. Other simple chemical modifications of the morphine molecule have yield many interesting drugs. Thus, one fruitful research area in the search for improved analgesics of high potency and/or lower dependance (addiction) liability has been the chemical modification of the morphine molecule.

In addition to modifying the morphine ring structure by chemical means, chemists have developed a second related field of research—the preparation of certain morphine part-structures—with the same end in mind as above; i.e., the synthesis of improved analgesic agonists and/or analgesic antagonists of improved properties. For example, meperidine, a widely used analgesic, can be written as a morphine part-structure. Many other morphine part-structures have been prepared, some of which have improved analgesic agonist properties and others, particularly those with an allyl group attached to a ring nitrogen, have opiate antagonist properties. It had been hoped that morphine part-structure research would produce a compound having both opiate agonist and antagonist properties since the opiate antagonist property would assure a user that the compound would have a greatly reduced dependance liability. Two recently marketed analgesics, pentazocine and phenazocine, fulfilled this hope at least in part since they are simultaneously antagonists and agonists, although still retaining a certain degree of opiate dependence liability.

One potential morphine part-structure can be written as a decahydroisoquinoline with an hydroxyphenyl group substituted on a ring junction carbon atom para to the isoquinoline nitrogen. An attempt to prepare such a compound was described by Boekelheide in a paper appearing in *J. Am. Chem. Soc.*, 69, 790 (1947). This paper set forth the preparation of what, according to the numbering system then in vogue, were 10-phenyl-decahydroisoquinolines. It was the author's conclusion, however, that the compound (IX) had a cis configuration and (footnote 5) showed low analgesic activity, a discouraging finding considering the complexity of the synthetic procedure. Sugimoto et. al., *J. Pharm. Soc. Japan*, 75 177 (1955), C.A. 1956 1814b described the synthesis of 8 or 10-alkylated decahydroquinolines. The reference also shows the afore-mentioned morphine part-structure, 10-(m-hydroxyphenyl)-3-methylisoquinoline [presently named as 1-methyl-3a-(m-hydroxyphenyl)-1,2-3,3a,4,5,6,7,7a,8-decahydroisoquinoline] but without furnishing a synthesis for it. These authors do not, in fact, describe the preparation of any decahydroisoquinoline, but describe only the preparation of the decahydroquinoline analogs.

Belgian Pat. No. 802,557, issued Jan. 19, 1974, discloses a general method of preparing N-substituted trans-3a-phenyldecahydroisoquinolines and specifically discloses trans-3a-(m-methoxy phenyl) and trans-3a-(m-hydroxyphenyl)-1-methyldecahydroisoquinolines, trans-3a-(m-methoxyphenyl) and trans-3a-(m-hydroxyphenyl)-1-phenethyldecahydroisoquinolines, and trans-1-cyclohexylmethyl-3a-phenyldecahydroisoquinoline. The synthetic procedure employed involves the catalytic reduction of the 7-7a double bond in, for example, a 1-alkyl-3a-phenyl (or substituted phenyl) 1,2,3,3a,4,5,6,8-octahydroisoquinoline. No new procedure for preparing the cis racemate is given.

Finch and coworkers *J. Org. Chem.*, 39, 1118 (1974) disclose trans-dl-1-methyl-3a-phenyl-1,2,3,3a,4,5,7a,8-octahydroisoquinoline (formula 2d, page 1119) and the corresponding cis-dl-1-methyl-3a-phenyldecahydroisoquinoline compound (formula 26, page 1120), the compound previously prepared by Boekelheide (loc. cit)—see also Boekelheide and Schilling, *J. Am. Chem. Soc.*, 72 712 (1950). The major part of the Finch et al publication, however, deals with an attempted preparation of the 5-hydroxy derivatives. Finch et al. use a different numbering system for the isoquinoline ring, using a naphthalene-type numbering rather than designating the ring nitrogen as position 1. Thus Finch et al. number the compounds as 2-methyl-4a-phenyl-6-hydroxy derivatives.

It is an object of this invention to provide active analgesics and analgesic antagonists belonging to the cis-decahydroisoquinoline series.

SUMMARY OF THE INVENTION

This invention provides cis-decahydroisoquinolines of Structure I below:

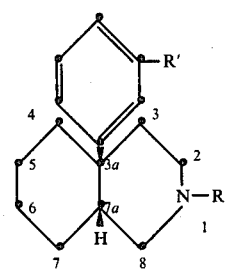

wherein
R is H, methyl or phenethyl;
R' is O—alkyl,

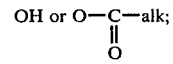

and alk is ($C_1$-$C_3$)alkyl.

Also included within the scope of this invention are pharmaceutically-acceptable acid addition salts of the above bases formed with non-toxic acids.

Compounds represented by the above formula are useful as analgesic agonists. Compounds of the above formula wherein R is H are in addition useful as intermediates in that they can be transformed into analgesically-active substances, as will be set forth hereinafter.

In the above formula, the term $(C_1-C_3)$alk, for which alk is the symbol, includes methyl, ethyl, isopropyl and n-propyl; thus, the term O-alk includes methoxy, ethoxy and the like. Similarly,

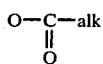

includes acetoxy, propionoxy and butyroxy. The pharmaceutically acceptable salts of the amine bases of this invention represented by the above formula are formed with nont-toxic acids, including, for example, salts derived from inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids including aliphatic mono and dicarboxylic acids, phenyl-substituted alkanoic acids, hydroxy alkanoic and alkandioic acids, aromatic acids, aliphatic and aromatic sulfonic acids, ets. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzeate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycollate, malate, tartrade, methanesulfonate, propanesulfonate, naphthalene-1-sulfonate, naphthalene-2-sulfonate and the like salts.

The bridgehead substituents, the phenyl at 3a and the hydrogen at 7a, in structure 1 have a cis relationship to one another; i.e., the two substituents are on the same "side" of the decahydroisoquinoline ring system, (cis). In addition, both the 3a and 7a carbon atoms are asymmetric, thus giving rise in each compound to 2 optical isomers, occurring as a racemate designated as the cis-dl-pair. Structure I is thus intended to comprehend both optical isomers of the cis-dl-racemate. Quantitative differences in analgesic agonist potency may exist between such enantiomorphs and we prefer the cis-1-compounds.

The compounds of this invention are prepared according to the following procedure, using the synthesis of compounds in which R' is methoxyl for purely exemplary pruposes:

2-(m-methoxyphenyl)cycloheptanone, a known compound, is alkylated with bromacetic ester in the presence of sodamide to yield 2-ethoxycarboylmethyl-2-(m-methoxyphenyl)cycloheptanone. Formylation with ethyl formate yields the 7-formyl derivative of 2-ethoxycarbonylmethyl-2-(m-methoxyphenyl)cycloheptanone. Reaction of this formyl compound with p-tosyl azide in the presence of diethylamine yields the corresponding 7-diaza compound. Irradiation of the diazaketone with ultraviolet light in a lower alkanol, for example, methanol, causes a rearrangement to take place. The product of this rearrangement, a cyclohexanecarboxylic acid derivative, is a 2-(m-methoxyphenyl)-2-ethoxycarbonylmethylcyclohexanecarboxylic acid ester. Hydrolysis of the diester with base yields a 1,3-diacid; i.e., 2-(m-methoxyphenyl)-2-carboxymethylcyclohexanecarboxylic acid. The diacid is obtained as a mixture of geometric isomers, cis and trans, in that both carboxyl groups can be on the same side of the cyclohexane ring (cis) or on opposite sides of the cyclohexane ring (trans). (Ordinarily, the cis and trans designation is based upon the orientation of the phenyl and hydrogen groups attached to the same carbons as the carboxylic acid and the carboxymethyl group). Two fractions, the cis and trans isomers, of the dicarboxylic acid are isolated and both subjected to treatment with acetyl chloride or other dehydrating agent to form the corresponding anhydride, named systematially as cis or trans-3,4,4a,5,6,7,8,8a-octahydro-1,3-dioxo-1H-2-benzopyran (VII). Reaction of the cis anhydride only with methylamine or with phenethylamine yields the corresponding dioxodecahydroisoquinoline (VIII). If methylamine is used to react with the anhydride, the product of the reaction is cis-1,2,3,3a,4,5,6,7,7a,8-decahydro-3a-(m-methoxyphenyl)-1,3-dioxo-1-methylisoquinoline. Reduction of the dioxo derivative with lithium aluminum hydride in THF or other suitable solvent yields the corresponding decahydroisoquinoline itself (IX) named, in the case where the N-substituent is methyl, as cis-dl-1-methyl-3a-(m-methoxyphenyl)-1,2,3,3a,4,5,6,7,-7a,8-decahydroisoquinoline. The methoxy derivative is converted to the corresponding m-hydroxyphenyl derivative by demethylation employing, for example, 48 percent hydrogen bromide in acetic acid as the demethylating reagent. The product of this reaction (X) is, again in the case where the N-substituent is methyl, named cis-dl-1-methyl-3a-(m-hydroxyphenyl)-1,2,3,3a,4-5,6,7,7a,8-decahydroisoquinoline. The above synthetic procedure is more fully set forth in Flow Sheet 1 which follows.

FLOW SHEET 1

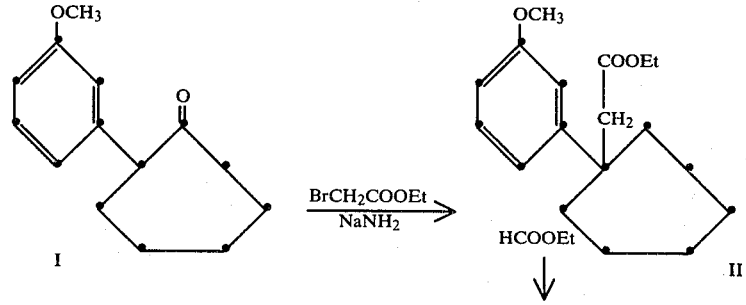

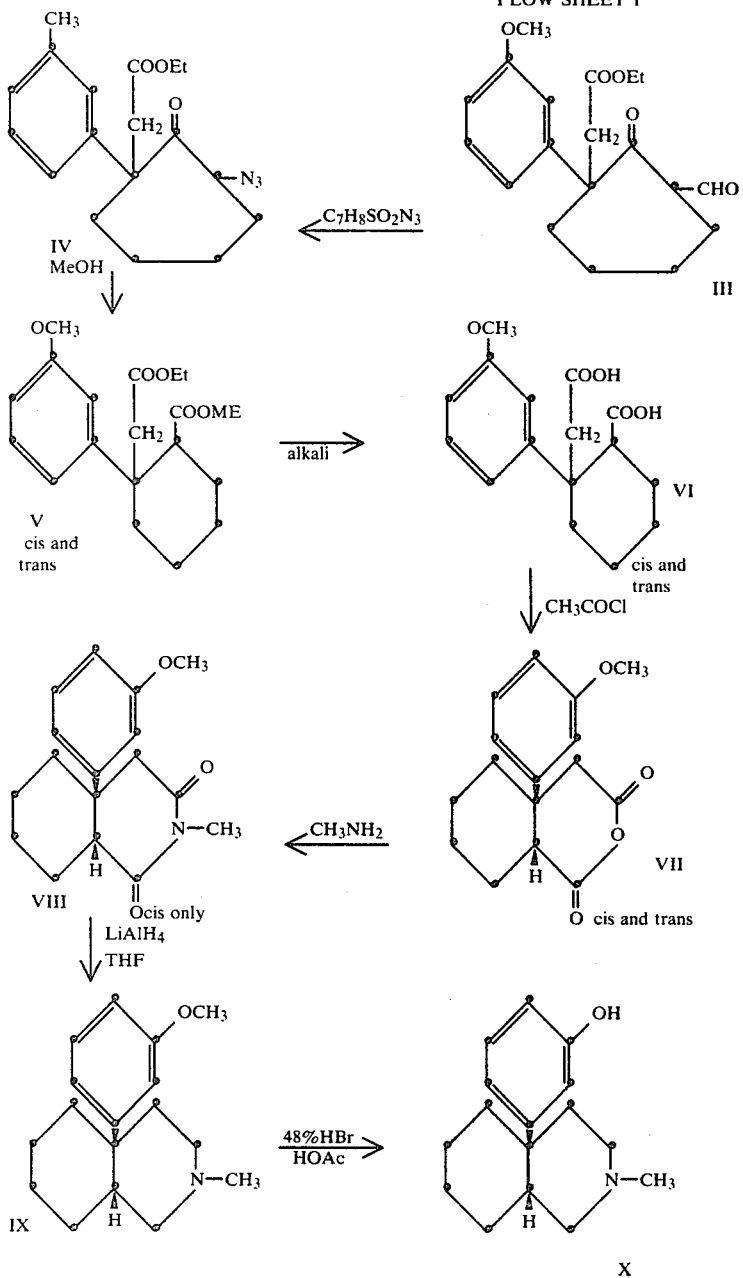

Compounds according to Formula I above in which R' is other than methoxyl or hydroxy are prepared either by using as a starting material the corresponding ethoxy or propoxy meta-substituted phenylcycloheptanone, prepared by the same procedure as the methoxy derivative. Compounds in which R' is lower alkanoyloxy are prepared by acetylation, propionylation or butyration of the corresponding m-hydroxyphenyl derivative, prepared as outlined above.

Alternatively, the N-phenethyl derivative can be prepared by demethylating cis-1-methyl-3a-(m-methoxyphenyl)-1,2,3,3a,4,5,6,7,7a,8-decahydroisoquinoline with phenyl chloroformate. Treatment of the resulting secondary amine with a phenethyl halide, such as phenethyl bromide, or with phenylacetylchloride followed by LiAlH₄ reduction of the thus-formed amide yields the desired N-phenethyl derivative (IX above in which the N-methyl is replaced by an N-phenethyl group). Demethylation of this compound, as with 48% HBr in acetic acid, yields cis-1-phenethyl-3a-(m-hydroxyphenyl)-1,2,3,3a,4,5,6,7,8-decahydroisoquinoline.

Salts of the free bases of this invention are prepared by dissolving the free base in ether and adding an equivalent of a suitable non-toxic acid, also in ether. The salts thus formed, as for example the sulfate and phosphate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo.

The compounds of this invention according to Structure I above can thus be prepared from compound XIII (Structure I wherein R is H and R' is methoxy) by alkylation as with methyliodide to yield the N-methyl compound or with phenethylbromide when the N-phenethyl compound is desired. Alternatively, the compound of Structure XIII can be acylated with phenylacetyl chloride or phenylacetic anhydride to yield the corresponding N-phenacyl derivative which, upon reduction with lithium aluminum hydride, yields the N-phenethyl derivative as before. In each instance, compounds according to Structure I in which R' is hydroxy can be prepared by demethylating the N-substituted derivative of compound XIII with 48% HBr in acetic acid and the like.

This invention is further illustrated by the following specific examples.

EXAMPLE 1

Preparation of
2-(m-Methoxyphenyl)-2-Ethoxycarbonylmethylcycloheptanone

A solution was prepared containing 181 g. of 2-(m-methoxyphenyl)cycloheptanone (prepared by the procedure of *Organic Syntheses*, Collective Volume IV, page 780) in 200 ml. of benzene. This solution was added in dropwise fashion to a stirred refluxing suspension of 43 g. of sodamide in 1500 ml. of benzene. After the addition had been completed, the reaction mixture was refluxed for an additional 2.5 hours, and was then chilled to about 0° C. A solution of 136 g. of ethylbromoacetate in 200 ml. of benzene was added in dropwise fashion. The resulting mixture was stirred overnight at ambient temperature, and was then poured into cold water. The benzene layer was separated and the aqueous layer extracted twice with equal volumes of benzene. The benzene layer and extracts were combined, washed with water until the washes were neutral to litmus and then dried. Evaporation of the solvent yielded 207 g. of a residue comprising 2-(m-methoxyphenyl)-2-ethoxycarbonylmethylcycloheptanone. The compound was purified by distillation, distilling at about 160° C. at a pressure of 0.1 mm./Hg.

Analysis Calcd.: C, 72.13; H, 7.65. Found: C, 72.47; H, 7.88.

EXAMPLE 2

Preparation of
2-(m-Methoxyphenyl)-2-Ethoxycarbonylmethyl-7-Formylcycloheptanone A mixture was prepared containing 313 g. of 2-(m-methoxyphenyl)-2-ethoxycarbonylmethylcycloheptanone, 2 liters of ether, 332.9 g. of sodium and 115.7 g. of ethyl formate. The reaction mixture was stirred at ambient temperature for five days and then poured onto ice water. The ether layer was separated and saved for recovery of starting material. The aqueous layer was acidified with cold 10 percent aqueous hydrochloric acid and the resulting acidic layer extracted with an equal volume of ether. The ether extract was separated, washed three times with a saturated aqueous sodium chloride solution and then dried. Evaporation of the solvent yielded 243 g. of 2-(m-methoxyphenyl)-2-ethoxycarbonylmethyl-7-formylcycloheptanone. Molecular ion by mass spectrograph 332.

Analysis Calcd: C, 68.66; H, 7.28. Found: C, 68.37; H, 7.56.

EXAMPLE 3

Preparation of
2-(m-Methoxyphenyl)-2-Ethoxycarbonylmethyl-7-Diazacycloheptanone

A solution was prepared containing 243 g. of 2-(m-methoxyphenyl)-2-ethoxycarbonylmethyl-7-formylcycloheptanone in 400 ml. of ether. A solution of 106 g. of diethylamine in 400 ml. of ether was added to the cycloheptanone derivative solution in dropwise fashion. The reaction mixture was stirred at ambient temperature for about 2 hours and then cooled to about 5° C. Next, a solution of 146 g. of p-toluenesulfonylazide in 400 ml. of ether was added in dropwise fashion. The reaction mixture was allowed to warm to ambient temperature and was stirred at that temperature for an additional five hours. The reaction mixture was then washed with water, and the ether layer separated and dried. Evaporation of the solvent under reduced pressure yielded 283 g. of 2-(m-methoxyphenyl)-2-ethoxycarbonylmethyl-7-diazacycloheptanone as an oil. Infrared spectrum of the oil showed a band at about 2075 cm$^{-1}$ characteristic of the diazaketone grouping.

EXAMPLE 4

Preparation of Methyl
2-(m-Methoxyphenyl)-2-Ethoxycarbonylmethylcyclohexanecarboxylate A solution was prepared from 283 g. of 2-(m-methoxyphenyl)-2-ethoxycarbonylmethyl-7-diazacycloheptanone in 1300 ml. of methanol. The solution was placed in a quartz vessel, the atmosphere flushed with nitrogen and a positive nitrogen pressure applied. The reaction mixture was then irradiated with ultraviolet light at 3,000 Å from a quartz lamp. Irradiation was continued until an aliquot sample taken from the reaction mixture gave no IR peak at 2075 cm$^{-1}$, indicative that there was no remaining diaza compound in solution. The product of the reaction, 2-(m-methoxyphenyl)-2-ethoxycarbonylmethylcyclohexanecarboxylate, produced by photolysis of the diazaketone was recovered as an oil weighing 272 g. upon evaporation of the solvent. The solvent was redissolved in ether and washed with aqueous sodium bicarbonate solution followed by water. The ether solution was separated, dried, and distilled. Upon distillation, fractions boiling in the range 190°–220° C. at 0.1 mm./Hg. and 220°–227° C. at 0.1 mm./Hg. were collected (total weight, 177 g.). The combined fractions were indicated by gas chromatography to contain 77 percent of the desired product. The combined products were therefore, redistilled through a short path vigreaux column to yield 2-(m-methoxyphenyl)-2-ethoxycarbonylmethylcyclohexanecarboxylate boiling at 178° C. at 0.05 mm./Hg. Yield: 116 g.

Analysis Calcd: C, 68.24; H, 7.84, Found: C, 68.15; H, 7.57.

EXAMPLE 5

Preparation of
2-(m-Methoxyphenyl)-2-Carboxymethylcyclohexanecarboxylic Acid 67 g. of methyl 2-(m-methoxyphenyl)-2-ethoxycarbonylmethylcyclohexanecarboxylate were mixed with 700 ml. of 5 percent aqueous potassium hydroxide in 900 ml. of dioxane. The reaction mixture was heated at refluxing temperature overnight and then cooled. Removal of the solvent in vacuo left an oily residue which was dissolved in water and the water layer extracted with ether. The ether layer was discarded. The aqueous layer was acidified with 10 percent aqueous hydrochloric acid. 2-(m-Methoxyphenyl)-2-carboxymethylcyclohexanecarboxylic acid being insoluble in the acidic aqueous layer separated and was extracted into ether. The ether layer was separated, washed with water and dried. Evaporation of the ether in vacuo left a semi-solid residue which crystallized in part upon addition of ether. About 19.2 g. of trans 2-(m-methoxyphenyl)-2-carboxymethylcyclohexanecarboxylic acid were obtained as a crystalline precipitate. Evaporation of ether from the filtrate yielded 35 g. of cis 2-(m-methoxyphenyl)-2-carboxymethylcyclohexanecarboxylic acid.

Analysis Calcd.: C, 65.74; H, 6.90. Found: C, 65.95; H, 6.66.

The above assignments of configuration (cis and trans) were based upon the ability of the particular isomer to form an imide by the reaction of Example 7 below.

EXAMPLE 6

Preparation of cis-3,4,4a,5,6,7,8,8a,-Octahydro-1,3-Dioxo-1H-2-Benzopyran

A solution of 35 g. of cis-2-(m-methoxyphenyl)-2-carboxymethylcyclohexanecarboxylic acid in 300 ml. of acetyl chloride was stirred at reflux temperature for about 4 hours. The reaction mixture was cooled, excess acetyl chloride removed by evaporation in vacuo and the residue comprising cis-3,4,4a,5,6,7,8,8a,-octahydro-1,3-dioxo-1H-2-benzopyran was purified by distillation; boiling point=210°-240° C. at 0.2 mm./Hg.

Analysis Calcd.: C, 70.06; H, 6.61. Found: C, 69.80; H, 6.41.

EXAMPLE 7

Preparation of cis-1,2,3,3a,4,5,6,7,7a,8-Decahydro-3a-(m-Methoxyphenyl)-1-Methyl-2,8-Dioxoisoquinoline A solution was prepared at −20° C. containing 13.7 g. of cis-3,4,4a,5,6,7,8,8a-octahydro-1,3-dioxo-1H-2-benzopyran in 200 ml. of toluene. A solution of methylamine in toluene was prepared by condensing methylamine gas at dry ice temperature and adding it at −20° C. to 100 ml. of toluene. The solution of cis-3,4,4a,5,6,7,8,8a-octahydro-1,3-dioxo-1H-2-benzopyran was added in dropwise fashion to the methylamine solution. An immediate oily precipitate occurred. After the addition had been completed, the reaction mixture was allowed to come to room temperature. The reaction mixture was then refluxed for about 24 hours using a Dean-Starke trap to collect water. After the theoretical amount of water (0.5 ml.) had been obtained, the reaction mixture was evaporated to dryness in vacuo. 200 ml. of 1 N aqueous sodium hydroxide were added to the residue, and the resulting mixture shaken and then heated gently for about five minutes. The reaction mixture was cooled to ambient temperature and extracted with ether. The ether layer was separated, washed with water, and with 5 percent aqueous hydrochloric acid. The ether layer was dried, and the ether evaporated therefrom to yield 9 g. of an oil comprising cis-1,2,3,3a,4,5,6,7,7a,8-decahydro-3a-(m-methoxyphenyl)-1-methyl-2,8-dioxoisoquinoline prepared in the above reaction.

Analysis Calcd.: C, 71.06; H, 7.37; N, 4.87. Found: C, 70.85; H, 7.10; N, 4.66.

Mass spectrographic analysis of the oil yielded a molecular ion of the calculated molecular weight (287).

EXAMPLE 8

Preparation of cis-dl-1,2,3,3a,4,5,6,7,7a,8-Decahydro-3a-(m-Methoxyphenyl)-1-Methylisoquinoline A solution was prepared from 16 g. of cis-1,2,3,3a,4,5,6,7,7a,8-decahydro-3a-(m-methoxyphenyl)-1-methyl-2,8-dioxoisoquinoline in 200 ml. of tetrahydrofuran. This solution was added in dropwise fashion to a stirred suspension of 4.1 g. of lithium aluminum hydride in 200 ml. of tetrahydrofuran. After the addition had been completed, the reaction mixture was refluxed for about five hours and then cooled to ambient temperature. 100 ml. of THF were added and 20 ml. of ethyl acetate to react with any excess lithium aluminum hydride present. A saturated aqueous solution of ammonium chloride was added in dropwise fashion until two phases separated, one organic and one aqueous. The reaction mixture was then filtered and the organic layer separated and evaporated to dryness in vacuo. The resulting residue was dissolved in ether, the ether layer washed with water and dried. Distillation of the residue yielded cis-dl-1,2,3,3a,4,5,6,7,7a,8-decahydro-3a-(m-methoxyphenyl)-1-methylisoquinoline boiling at about 180° C. at 0.05 mm. of mercury.

The hydrochloride salt was prepared by dissolving the decahydroisoquinoline in ether and adding gaseous hydrogen chloride. The hydrochloride salt was separated by filtration and recrystallized from a 50:50 isopropyl alcohol-isopropyl ether solvent mixture. M.P.=220°-2° C.

Analysis Calcd.: C, 69.02; H, 8.86; N, 4.73; Cl, 11.98. Found: C, 68.75; H, 8.90; N, 4.80; Cl, 11.86.

EXAMPLE 9

Preparation of cis-dl-1,2,3,3a,4,5,6,7,7a,8-Decahydro-3a-(m-Hydroxyphenyl)-1-Methylisoquinoline About 2.7 g. of cis-dl-1,2,3,3a,4,5,6,7,7a,8-decahydro-3a-(m-methoxyphenyl)-1-methylisoquinoline were dissolved in 20 ml. of glacial acetic acid containing 20 ml. of 48 percent hydrogen bromide. The reaction mixture was heated with stirring at reflux temperature for about 15 hours and was then cooled. The pH of the solution was adjusted to about 10.2 while the solution was being stirred and cooled by the addition of 50 percent aqueous sodium hydroxide. cis-dl-1,2,3,3a,4,5,6,7,7a,8-decahydro-3a-(m-hydroxyphenyl)-1-methylisoquinoline, being insoluble in alkali at that pH separated and was extracted into a mixture of n-butanol and benzene. The organic layer was separated and dried. Evaporation of the solvent yielded an oil. The oily residue, containing the N-methyl decahydroisoquinoline, was converted to the hydrochloride salt which was not crystalline. The salt was reconverted to the free base and the free base dissolved in ethyl acetate. An equimolar amount of maleic acid, also in ethyl acetate, was added and the corresponding maleate salt formed. cis-dl-1,2,3,3a,-4,5,6,7,7a,8-Decahydro-3a-(m-hydroxyphenyl)-1-methylisoquinoline maleate thus prepared melted at 135°-138° C. from ethyl acetate.

Analysis Calcd.: C, 66.46; H, 7.53; N, 3.88. Found: C, 66.69; H, 7.29; N, 3.39.

EXAMPLE 10

Alternate Preparation of cis-dl-3a-(m-Methoxyphenyl)-1-Methyl-1,2,3,3a,4,5,6,7,7a,8-Decahydroisoquinoline A solution containing 1.7 g. of cis-1-methyl-3a-(m-methoxyphenyl)-2,8-dioxo-1,2,3,3a,4,5,6,7,7a,8-decahydroisoquinoline furnished by the procedure of Example 7 in 20 ml. of THF was added in dropwise fashion to a stirred suspension of 0.45 g. of lithium aluminum hydride and 20 ml. of THF. The reaction mixture was heated at reflux temperature for five hours and then allowed to stir at ambient temperature overnight. 40 ml. of THF were added and 10 ml. of ethyl acetate in dropwise fashion to decompose any unreacted lithium aluminum hydride. Next, sufficient saturated aqueous ammonium chloride solution was added until a precipitate appeared. The reaction mixture was filtered and the filtrate evaporated to dryness in vacuo. The residue was dissolved in ether and the ether solution washed with water, dilute aqueous hydrochloric acid and with water. The ether layer was separated and discarded. The aqueous acidic layer containing cis-dl-3a-(m-methoxyphenyl)-1-methyl-1,2,3,3a,4,5,6,7,7a,8-decahydroisoquinoline formed in the above reduction as the hydrochloride salt was made basic with 10 percent aqueous sodium hydroxide. The decahydroisoquinoline, being insoluble in the aqueous alkaline layer, separated and was extracted with ether. The ether layer was separated, washed with water until the washes with neutral to litmus, and then dried. Evaporation of the solvent in vacuo yielded 1 g. of an oil. cis-dl-3a-(m-methoxyphenyl)-1-methyl-1,2,3,3a,4,5,6,7,7a,8-decahydroisoquinoline thus prepared was identical to the product prepared by the procedure of Example 8.

EXAMPLE 11

Isomerization of Trans-1-Methyl-3a-(m-Methoxyphenyl)-2,8-Dioxo-1,2,3,3a,4,5-6,7,7a,8-Decahydroisoquinoline A solution of 2 g. of trans-1-methyl-3a-(m-methoxyphenyl)-2,8-dioxo-1,2,3,3a,4,5,6,7,7a,8-decahydroisoquinoline in 40 ml. of dioxane was mixed with 24 ml. of 30 percent aqueous potassium hydroxide and the resulting mixture heated at refluxing temperature for 30 minutes. The volatile substitutents were removed by evaporation to dryness and the residue dissolved in ether. The ether layer was separated, washed with water and dried. Evaporation of the ether in vacuo yielded 1.7 g. of cis-1-methyl-3a-(m-methoxyphenyl)-2,8-dioxo-1,2,3,3a,4,5,6,7,7a,8-decahydroisoquinoline produced in the above reaction. NMR spectrum of the product showed that it was identical with the cis fraction from Example 8 and different from the trans starting material.

EXAMPLE 12

Preparation of cis-dl-3a-(m-Methoxyphenyl)-1,2,3,3a,4,5,6,7,7a,8-Decahydroisoquinoline A solution of 10.99 of phenylchloroformate in 25 ml. of methylene dichloride was added in dropwise fashion at ambient temperature to a solution of 17 g. of cis-dl-1-methyl-3a-(m-methoxyphenyl)-1,2,3,3a,4,5,6,7,7a,8-decahydroisoquinoline in 200 ml. of methylene dichloride in a 500 ml., 3-neck flask equipped with stirrer, dropping funnel and condenser. After the addition had been completed, the reaction mixture was refluxed for 4 hrs. and then allowed to stand overnight at room temperature. The solvent was removed by evaporation in vacuo. 100 ml. of 5 Percent aqueous sodium hydroxide were added to the resulting residue, and the resulting mixture heated with stirring. cis-dl-1-Phenoxycarbonyl-3a-(m-methoxyphenyl)-1,2,3,3a,4,5,6,7,7a,8-decahydroisoquinoline, formed by the above series of reactions, was insoluble in aqueous base and was extracted with 1 l. of ether. The ether layer was separated, washed with 500 ml. portions of water and saturated aqueous sodium chloride and dried. The solvent was evaporated in vacuo and the resulting residue dissolved in 1 l. of ether. The ethereal solution was washed successively with 250 ml. portions of 10 percent hydrochloric acid, saturated aqueous sodium chloride and water. The ethereal solution was dried and the ether removed therefrom in vacuo. The resulting residue, comprising the phenyl carbamate, was heated with 200 ml. of 50 percent aqueous potassium hydroxide and 750 ml. of ethanol. The resulting mixture was heated to refluxing temperature for 60 hrs. The reaction was cooled to ambient temperature, and the solvent removed by evaporation. The residue, comprising the hydrolysed product cis-dl-3a-(m-methoxyphenyl)-1,2,3,3a,4,5,6,7,7a,8-decahydroisoquinoline, was diluted with 250 ml. of water. The aqueous layer was made acidic by the addition of 12 N hydrochloric acid. The acidic aqueous layer was washed with 1 l. of ether and the ether discarded. The acidic aqueous layer was then made strongly basic. The decahydroisoquinoline, being insoluble in the alkaline layer, separated and was extracted into two 750 ml. portions of ether. The ether extracts were combined and the combined extracts washed with three 600 ml. portions of saturated aqueous sodium chloride followed by one 500 ml. water wash. The ethereal solution was dried and the ether removed therefrom in vacuo, leaving as a residue purified cis-dl-3a-(m-methoxyphenyl)-1,2,3,3a,4,5,6,7,7a,8-decahydroisoquinoline.

EXAMPLE 13

Preparation of cis-dl-1-Phenethyl-3a-(m-Methoxyphenyl)-1,2,3,3a,4,5,6,7,7a,8-Decahydroisoquinoline The following ingredients were introduced into a 250 ml. 3-neck round bottom flash equipped with stirrer, condenser and dropping funnel: 3.89 of cis-dl-3a-(m-methoxyphenyl)-1,2,3,3a,4,5,6,7.7a,8-decahydroisoquinoline, 26 g. potassium carbonate, 59 ml. methanol and 17.7 g. water. The mixture was chilled to about 0° C., and 2.89 g. of phenylacetyl chloride were thereto added in dropwise fashion. The reaction mixture was stirred for one hour in the range −5° C. to 0° C. and for one hour at ambient temperature. Volatile constituents were removed by evaporation in vacuo. The resulting residue containing cis-dl-1-phenylacetyl-3a-(m-methoxyphenyl)-1,2,3,3a,4,5,6,7,7a,8-decahydroisoquinoline formed in the above reaction was extracted with two 500 ml. portions of ether. The ether extracts were combined and the combined extracts washed successively with two 100 ml. portions of 5 percent aqueous sodium bicarbonate, with 10 percent hydrochloric acid and with water, and then dried. Evaporation of the ether left as a residue the purified 1-phenyl acetyl derivative which was dissolved in 50 ml. of anhydrous THF. The THF solution was added to a suspension of 4 g. of LiAlH₄ in 150 ml. THF. The resulting mixture was heated at reflux for 4 hrs. About 50 ml. of ethyl acetate were added to react with excess LiAlH₄ followed by sufficient ammonium tartrate to precipitate inorganic salts present. The THF layer was separated by decantation. The residual salts were washed with THF and the wash again separated by decantation. The THF solution and washes were combined, and the THF removed by evaporation. The resulting residue, comprising cis-dl-1-phenethyl-3a-(m-methoxyphenyl)-1,2,3,3a,4,5,6,7,7a,8-decahydroisoquinoline formed in the above reduction, was dissolved in ether and the ether layer washed with water followed by saturated aqueous sodium chloride and then dried. Evaporation of the ether yielded 4.5 g. of cis-dl-1-phenethyl-3a-(m-methoxyphenyl)-1,2,3,3a,4,5,6,7,7a,8-decahydroisoquinoline as an oil.

The hydrobromide salt was prepared by addition of 48 percent aqueous HBr to an ethereal solution of the base in dropwise fashion until the solution was just blue to congo red paper. Evaporation of the solvent yielded a solid white residue comprising cis-dl-1-phenethyl-3a-(m-methoxyphenyl)-1,2,3,3a,4,5,6,7,7a,8-decahydroisoquinoline hydrobromide which melted at 223°–4° C. after recrystallization from an isopropanol-diisopropyl ether solvent mixture.

Analysis Calcd.: C, 66.97; H, 7.49; N, 3.25; Br, 18.56. Found: C, 66.77; H, 7.27; N, 3.49; Br, 18.31.

EXAMPLE 14

Preparation of cis-dl-1-Phenethyl-3-(m-Hydroxyphenyl)-1,2,3,3a,4,5,6,7,7a,8-Decahydroisoquinoline About 1.6 g. of cis-dl-1-phenethyl-3a-(m-methoxyphenyl)-1,2,3,3a,4,5,6,7,7a,8-decahydroisoquinoline were mixed with 12 ml. each of glacial acetic acid and 48 percent aqueous HBr, and the mixture heated at reflux temperature for 15 hrs. The reaction mixture was cooled and then poured over an excess of ice. Sufficient 50 percent aqueous sodium hydroxide was added to bring the pH to about 10.2, cis-dl-1-phenethyl-3a-(m-hydroxyphenyl)-1,2,3,3a,4,5,6,7,7a,8-decahydroisoquinoline, formed in the above demethylation, separated as an oil and was extracted with a 3:1 n-butanol-benzene solvent mixture. The organic extract was separated and washed successively with water (multiple washes) and saturated aqueous sodium chloride (twice) and then dried. Evaporation of the solvent yielded about 1 g. of an oil comprising cis-dl-1-phenethyl-3a-(m-hydroxyphenyl)-1,2,3,3a,4,5,6,7,7a,8-decahydroisoquinoline.

The hydrochloride salt was prepared by adding a saturated solution of HCl in ether to an ethereal solution of the base in dropwise fashion until congo red paper gave a just-positive (blue) reaction. Recrystallization from an isopropanol-diisopropyl ether solvent mixture yielded 0.5 g. of a crystalline solid melting at 126° C. with decomposition.

As previously stated, the compounds of this invention are analgesic agonists and are capable of producing profound, opiate-like analgesia in mammals. The compounds demonstrate their analgesic agonist activity in the mouse-writhing test and in the rat tail jerk assay, both standard assays for analgesic action. In the mouse writhing assay, the following E.D.$_{50}$'s (dose which decreases the number of writhing observations by 50 percent compared to controls) were obtained for the compounds of this invention as follows:

cis-dl-1-methyl-3a-(m-hydroxyphenyl)-1,2,3,3a,4,5,6,7,7a,8-decahydroisoquinoline oxalate $E.D._{50} \cong 2.0$ mg./kg. subcutaneously
$\cong 10$ mg./kg. orally cis-dl-1-methyl-3a-(m-methoxyphenyl)-1,2,3,3a,4,5,6,7,7a,8-decahydroisoquinoline hydrochloride $E.D._{50} \cong 4$ mg./kg. subcutaneously
$\cong 6$ mg./kg. orally The compounds failed to block the straubed tail in mice produced by subcutaneous injection of morphine, indicating an absence of morphine antagonist properties.

In the rat tail jerk assay, compounds of this invention also demonstrated analgesic agonist activity as follows:

cis-dl-1-methyl-3a-(m-hydroxyphenyl)-1,2,3,3a,4,5,6,7,7a,8-decahydroisoquinoline oxalate gave increased reaction times at a 0.5–10 mg./kg. subcutaneous dosage when measured 30 minutes after injection. By the oral route, dosages of from 10–20 mg./kg. measured at times varying from 15 minutes to 2 hours after injection also gave statistically significant increases in reaction times. Naloxone blocked this activity. The corresponding methoxy derivative, cis-dl-1-methyl-3a-(m-methoxyphenyl)-1,2,3,3a,4,5,6,7,7a,8-decahydroisoquinoline as the hydrochloride salt shows opiate-like analgesic activity in the same assay at dose levels from 2–20 mg./kg. subcutaneously and from 2–20 mg./kg. orally.

The compounds of this invention can be employed to produce analgesia in mammals by administration via either the parentereal or oral route. For oral dosage, a suitable quantity of a pharmaceutically-acceptable salt of a base according to Formula I, formed with a non-toxic acid, is mixed with starch or other excipient, and the mixture placed in telescoping gelatin capsules each containing an analgesic dose. Similarly, the salt can be mixed with starch, a binder, a lubricant, and the mixture compressed into tablets each containing a standard analgesic dose. The tablets may be scored if lower or divided dosages are to be used. With parenteral administration, the intramuscular or subcutaneous routes are preferred. For this purpose, aqueous solutions or suspensions are employed using a pharmaceutically-acceptable salt of the amine base of formula 1. In general, modes of administration and pharmaceutical forms found useful in the pase for morphine, codeine, methadon, meperidine and other opiate-like analgesics can be adopted by those skilled in the art for the compounds of this invention.

We claim:

1. A compound of the formula:

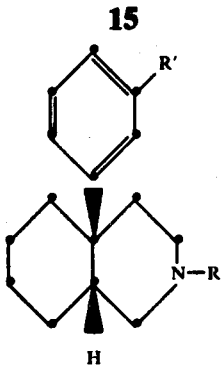

wherein

R is methyl;
R' is O-alk or OH; and
alk is ($C_1$–$C_3$) alkyl, and pharmaceutically-acceptable salts thereof formed with non-toxic acids.

2. A compound according to claim 1, said compound being cis-dl-1-methyl-3a-(m-methoxyphenyl)-1,2,3,3a,4,5,6,7,7a,8-decahydroisoquinoline.

3. A compound according to claim 1, said compound being cis-dl-1-methyl-3a-(m-hydroxyphenyl)-1,2,3,3a,4,5,6,7,7a,8-decahydroisoquinoline.

4. cis-dl-3a-(m-hydroxyphenyl)-1,2,3,3a,4,5,6,7,7a,8-decahydroisoquinoline.

* * * * *